United States Patent [19]

Moore et al.

[11] 4,228,810

[45] Oct. 21, 1980

[54] CARE AND TREATMENT OF CURLY HUMAN HAIR

[75] Inventors: Edward R. Moore, Princeton; Eldred O. Riddle, Brooklyn Park, both of Minn.

[73] Assignee: La Maur Inc., Minneapolis, Minn.

[21] Appl. No.: 961,917

[22] Filed: Nov. 20, 1978

[51] Int. Cl.$^3$ .............................................. A45D 7/00
[52] U.S. Cl. .................................................... 132/7
[58] Field of Search .................... 132/7; 424/71–72

[56] References Cited

U.S. PATENT DOCUMENTS

| | | | |
|---|---|---|---|
| 3,227,615 | 1/1966 | Korden | 132/7 |
| 3,560,609 | 2/1971 | Korden | 132/7 |
| 3,847,165 | 11/1974 | Patel | 132/7 |
| 4,036,241 | 7/1977 | Karg | 132/7 |
| 4,038,995 | 8/1977 | Edelberg | 132/7 |
| 4,134,411 | 1/1979 | Yamazaki | 132/7 |

*Primary Examiner*—G. E. McNeill
*Attorney, Agent, or Firm*—Arthur S. Caine

[57] ABSTRACT

Curly or kinky human hair is permanently relaxed into a relatively smoothed or S-curved condition by a series of treatments involving application of a non-injurious composition containing a water solution of a salt of a weak acid to disrupt internal bonds of the hair, while manipulating and straightening the hair, then removing and replacing the first composition with a fixative to reconstruct or modify the structure of the hair, and finally applying a stabilizing composition which also acts to set and condition the hair.

3 Claims, No Drawings

CARE AND TREATMENT OF CURLY HUMAN HAIR

This invention relates to improvements in the care and treatment of curly human hair. Kinks and curls in human hair are inherited traits and are attributable to irregular bonding of internal portions of the hair. In order to style kinky or curly hair, it is frequently first necessary to straighten this hair to some degree. This procedure is commonly referred to as "relaxing" the hair, and has been accomplished to some degree in the past by first disrupting the internal bonds of the hair and then manipulating or extending the hair to some degree of straightness; and then, hopefully, rebuilding the internal bonds of the hair in order to prevent eventual reversion to the kinky or curly state.

The most popular method currently employed to treat the hair while it is still growing from the head is to use a solution of sodium hydroxide or lye; while another method has been with the use of ammonium thioglycolate, commonly used in the past for producing a "cold permanent wave".

The relaxing effect obtained from the use of ammonium thioglycolate is frequently insufficient, particularly on kinky hair, and in general, it has been found that there is a fair possibility of eventual reversion. On the other hand, with the use of sodium hydroxide or lye there is considerable danger of damage to the scalp, as well as the hair, and retreatment may produce breakage of the hair at the junction between the new growth and the previously treated hair shafts. Considerable care must be exercised to make certain that there are no abrasions or sores on the scalp that would permit the lye to enter below the skin to cause burns, and in fact, a base, such as petroleum jelly, is generally applied to protect the scalp before the treatment with the lye solution.

The present invention obviates the problems aforenoted. Re-treatment of hair previously straightened, using the teachings herein, may be accomplished without limitation and reservation. Treatment by the described method, and employing the described composition, may be repeated as desired, even if immediately subsequent to prior treatment. The new compositions cause no significant skin or scalp pain or discomfort, or irritation for those with normal, healthy, scalp conditions. In fact, before the curl-relaxing treatments of the present invention, the person undergoing treatment may be given a shampoo to thoroughly cleanse the hair and the scalp, in contrast to the application of protective coating, such as petroleum jelly, as practiced heretofore.

This new technique for relaxing or diminishing of the kinks or curls from hair is the more astonishing when it is realized that those skilled in the art, including those who market the current commercial strongly alkaline treatments, have had available to them for several decades each of the significant chemicals employed in formulating the compositions taught herein. Despite that knowledge, no one has heretofore, insofar as is known, discovered or presented the industry with any practical and effective alternative to the strong alkaline approach aforenoted. Thus, this invention constitutes a breakthrough in that respect, in that for the first time, it provides a safe and painless technique for treating natural kinks and curls in hair, and fixing the hair in a relatively straightened condition, while simultaneously preserving, or imparting "liveliness" and "buoyancy" and "manageability" to the hair.

In general, the new method for treating natural human hair on the head, to remove or reduce relatively severe kinks or curls, involves the following procedure:

Pre-treatment

Cleansing the Hair and Scalp

In contrast with the procedure required in the treatment with lye, the hair and scalp should preferably be clean and free, not only of grease or other protective coatings, but also any normal soil, such as atmospheric dust, dried perspiration, or any form of previously used hair care composition. To that extent, the hair and scalp should be properly shampooed, thoroughly rinsed and towel dried, so that the following treatment will apply equally to all of the hair on the scalp.

Treatment

A. To clean hair is applied a curl relaxing composition containing essentially a solution of a salt of an acid capable of reducing the cystine-linkages of hair keratin. The composition contains a water solution of ammonium bisulfite buffered to produce a pH less than 7, but more than 5. The solution must be applied to the hair in such a manner as to saturate the hair. This can be accomplished by directly applying the liquid and then thoroughly working it into the hair with repeated combings to extend the hair; or it may be accomplished by applying the liquid to a fabric or spongy material that overlies the hair and would tend to saturate the hair; however, an easy manner of providing the necessary stable condition is to combine the solution with a material to form a gel-like composition which not only makes application easy to adhere to the hair, but which also has an added advantage in lending body to the hair that aids in the subsequent straightening action. The gel-like consistency may be accomplished by the addition of an inert thickener. The water content of the composition should exceed 50% of the total bulk of the gel, and the inert thickener should preferably be present in an amount to cause the viscosity of the gel to be between 80,000 and 400,000 centipoises at 25° C. Other ingredients may optionally be included and the composition's pH must be on the acid side, but not below about 5.7.

The ammonium bisulfite severs the disulfide-linkages (KSSK) in keratin, and is also believed to convert one of the sulfurs of the cystine-linkage into a sulfhydryl group (KSH). It is believed to form a Bunte salt ($KSSO_3^-  + NH_4^+$) with the other sulfur of the cystine-linkage. The thickener in the composition functions as an inert bonding material for holding strands of curly hair in a somewhat stretched and straightened condition against each other and against the scalp.

A specific illustrative relaxer gel formula in percent by weight is as follows:

55.55—deionized water;

22.00—ammonium bisulfite at 47% concentration dissolved in water;

2.50—hydroxy ethyl cellulose as the inert water soluble organic thickener;

10.00—urea (which breaks down under heat and buffers the pH to 6.2, and also contributes to cause swelling of hair strands for more effective action by the ammonium bisulfite);

5.00—isopropanol, 99% anhydrous (which helps in wetting the hair fibers);
1.14—dibasic sodium phosphate (a hydrogen ion contributor which also influences pH);
0.46—citric acid (buffers pH);
1.10—aqua ammonium (buffers pH);
0.05—chelating agent;
0.0001—organic dye (simply for color tint);
0.20—perfume;
2.00—non-ionic surfactant, present merely to solubilize the perfume Blending of this composition in a homogenous mass is illustratively accomplished by dissolving, in the water, the chelating agent, the sodium phosphate, citric acid, urea, and the hydroxy ethyl cellulose. Heating the mixture to about 45° C. facilitates solubilization of the cellulose thickener. After cooling to about 25° C., the organic dye dissolved in isopropanol is added, then a blend of the ammonium bisulfite and ammonia is added. Finally, the perfume blended with the nonionic surfactant is added. Thorough mixing is conducted at each addition so as to blend the ingredients into a homogenous mass.

The hair is prepared for receiving the composition by parting the hair from front to back, and from ear to ear, creating four sections. The relaxing composition is applied to the root areas of the hair, beginning with the back sections and advancing towards the crown, and then to the front sections, leaving the hairline until last. The curl relaxing composition is applied to the hair, working outwardly from the root portions, and then throughout the hair strands by hand molding, and combing of the hair into a stretched relatively straight condition, with the hair pasted against the scalp. If the hair is long, it should be folded and placed on top of the head.

B. The molded hair is subjected to a heat treatment while substantially maintaining the moisture content of the composition in the hair by covering the head with a plastic cap composed of polyethylene, or similar plastic material, so that it serves as a barrier to water escape. The molded covered hair is then subjected to a heat treatment by surrounding the covered head with a conventional heating hair dryer capable of heating the molded hair above 38° C. and up to about 50° C. Heat is applied in this manner for a period between 5 and 20 minutes, and the time is determined by periodically removing the plastic cap, and examining or testing a strand of hair to determine the effect of the relaxing composition.

When the visual results of the test seem acceptable, the flexible plastic covering is removed and the warm hair with the relaxing composition therein is further worked by hand, smoothing of it, and combing through the hair from the root areas, and subsequently turning the comb to create tension on the hair. This working and combing operation should be conducted for about 20 minutes, or until the hair is relaxed to the degree desired. A visual test of the curl relaxation is that if a portion of the strand of hair adjacent the scalp remains against the scalp, the hair will be generally sufficiently relaxed. Additionally, a strand of hair, wiped free of composition, using a wet towel, may be rested on the palm of one's hand to observe its degree of relaxation before terminating this post-heat treatment.

Next, the hair and scalp are thoroughly rinsed with tepid water, and then towel blotted to a damp condition. In general, rinsing should extend for as much as 5 minutes.

C. The relaxed hair keratin is then subjected to a fixative treatment which involves applying and working into the hair a composition having an alkaline pH not greater than about 9. As in the case of the relaxing composition, the fixative must also be applied in a manner as to saturate the hair, which may be accomplished through the same procedure used in applying the relaxing fluid, or it may also be combined with an inert thickener to give a gel-like consistency, and thus simplifying application to the hair.

A specific illustrative fixative of a gel formula is prepared as follows:
89.55—deionized water;
5.00—sodium bicarbonate as the weak acid salt;
2.50—hydroxy ethyl cellulose as the inert water soluble thickener;
0.05—sodium hydroxide (for adjusting pH);
0.20—chelating agent (trisodium hydroxyethyl ethylenediamine-triacetate) for counter-acting metal impurities;
2.00—non-ionic surfactant (polyethylene [23] lauryl ether) a solubilizer for the preservatives;
0.70—preservatives, including bactericides and fungicides, methyl parasept, propyl parasept, umidazolidinyl urea.

The buffering of this composition gives it a pH of about 8.2. Its viscosity at 25° C. is about 250,000 centipoises.

In this composition, the water serves as a vehicle for ionization of the weak acid salt. Illustrative of such salts, exhibiting an alkaline pH below about 9, are sodium bicarbonate (i.e. baking soda), ammonium bicarbonate, disodium phosphate, and the like. They contain oxygen in their anion; and the acid hydrogen present is weaker than the alkaline or base strength of the basic radical or cation. The function of the weak acid salt seems to be that of reacting with the Bunte salt complex formed at some of the sulfurs of the several cystine-linkages during the relaxation step. The reaction is complex but, aside from by-products later rinsed out of the hair, is believed to cause the Bunte salt complexes to be converted to sulfhydryl groups (KSH), thereby increasing the sulfhydryl groups beyond that attainable with the above relaxer treatment alone. The fixative treatment at least contributes to further alteration of the severed disulfide-linkages of the hair keratin, with the formation of additional sulfhydryls being the most plausible explanation from an empirical standpoint. The function of the organic thickener in this fixative treatment is that of cooperatively working with the weak acid base for enhancing a straightened condition for the hair strands. The fixative treatment contributes to re-orientation of the hair keratin toward a relaxed straightened condition for the strands of hair, and additionally obstructs recombination of several cystine-linkages back to their original condition.

Blending of this composition is accomplished by dissolving the sodium bicarbonate in the water and then adding the other ingredients, with continued mixing, while the mass is heated to 55°-60° C. until homogeneity is reached, after which it is cooled to ambient temperature.

The fixative composition is applied to the hair at normal room temperature and thoroughly worked into the hair, including the root portions. It is allowed to remain on the hair for about 5 to 10 minutes, after which it is thoroughly rinsed from the hair with tepid water. The hair is then towel blotted to a state of semi-dryness.

D. Following the fixative treatment, the hair is treated to stabilize its condition. Stabilization is accomplished by the application of a bonding lotion which essentially contains a water soluble thermosetting aminopolyamide-epichlorohydrin resin that alters the hair keratin sulfhydryls and prevents subsequent recombination of the cystine-linkages which had been severed by the relaxing composition.

A specific illustrative formula in weight percent is as follows:

95.60—deionized water;
2.00—resin ("Delsette" by Hercules) low molecular weight form of adipic acid-diethylene-triamine polyamide reacted with epichlorohydrin and secondary amines to give azetidinium functional groups which react with sulfhydryl;
2.00—quaternized vinylpyrrolidone copolymer (this optional ingredient contributes to hair manageability);
0.30—nonionic surfactant, polyoxyethylene (9) octylphenyl ether;
0.05—perfume fragrance;
0.05—preservative-formalin.

The stabilizing composition may be combined at ambient temperature. The composition is thoroughly worked into the hair and is permitted to remain on the hair to aid in setting and stabilizing the hair. This composition, apart from the high water content, is primarily resinous. The only essential resin is the aminopolyamide-epichlorohydrin. As used herein, and in the claims "aminopolyamide-epichlorohydrin" resin means the water-soluble polymeric reaction product of epichlorohydrin and a polyamide derived from a polyalkylene polyamine and a $C_3$–$C_7$ saturated aliphatic dicarboxylic acid. These resins are disclosed, and their method of preparation is taught by Maria A. Korden in U.S. Pat. No. 3,227,615, issued Jan. 4, 1966, here incorporated by reference. In brief, preparation of these resins involves first reacting one or more of the dicarboxylic acids with one or more of the polyalkylene polyamines under conditions such as to produce a water-soluble polyamide containing the recurring groups —NH($C_nH_{2n}$HN)$x$——CORCO— where n and x are each 2 or more and R is the divalent hydrocarbon radical of the dicarboxylic acid. This water-soluble polyamide is then reacted with epichlorohydrin to form the water-soluble cationic thermosetting resin. The epichlorohydrin reacts with the secondary amines of the water-soluble polyamide to produce azetidinium functional groups, or equivalent groups, which react with the sulfhydryl formed in the hair keratin.

In the present invention, the large number of sulfhydryl sites created in the hair keratin contributes to a massive addition of the complex polyamide-epichlorohydrin resin as part of the complex keratin of the hair, giving it body and manageability as well as almost totally preventing reversion to its original curly state. In essence, the hair is permanently placed in the straightened condition the subject desires. Generally, this straightened condition will approximate an open or loose S-curve for the strands of hair, which is easier to manage. The hair may then be styled, or even curled to various degrees in different parts to satisfy the desires of individual taste.

In the application of this invention to the relaxing of kinky or curly hair, there is considerable latitude in the manipulation of the hair, depending upon the degree of curliness of the hair, which will seldom be the same for any two people.

In a preferred form, the relaxing composition is composed as a gel, which is thoroughly worked into the hair by means of hand molding and combing the hair into a stretched relatively straight condition. The step of enclosing the molded hair in a moisture impervious cap, and then subjecting it to mild heating is very important, for apparently heat accelerates the chemical reaction between the composition and the hair. The extent of heating is, of course, dependent upon the degree of curliness or resistance of the hair. However, it is of considerable importance to smooth and straighten the hair with comb and hands while the hair is still warm. The smoothing action should start at the roots of the hair, using the thumbs and the flat back portion of the comb. The comb should have its tines turned upward to create some tension on the hair. In following this procedure, it can be seen whether or not the proper degree of straightening has occurred. If not, the plastic cap can be put over the head again, and the heating action continued, for this process is not harmful to the hair. While the thickener is inert chemically, it cooperates in effecting the straightening of the hair by adding body to the hair.

Hair which has been treated according to this invention may be set by using any procedure. It will smooth and tend to straighten all types of naturally curly hair, and it is safe to repeat treatments as new growth occurs.

That which is claimed is:

1. A method of permanently relaxing natural curls from hair on a human head, comprising:
  (a) applying to said hair, including the root scalp portions of the hair, a curl relaxing composition comprising a blend of water and a salt of an acid having a pH less than 7, but more than 5, and having the capacity of reducing the disulfide linkages of the hair keratin, while manipulating the treated hair by hand action and combing into a relatively straightened condition;
  (b) submitting said treated hair to a heat treatment at a temperature above human body temperature while simultaneously maintaining the moisture content of the treated hair substantially constant until said hair exhibits a relaxed condition;
  (c) water rinsing said relaxing composition from the hair and scalp and subsequently removing said water to at least a towel blotted state;
  (d) applying to the relaxed hair a fixative composition, comprising a blend of water and a weak alkaline substance, having a pH not greater than about 9, and having the capacity of chemically neutralizing the relaxing composition;
  (e) water rinsing the fixative composition from the hair and subsequently removing said water to at least a towel blotted state; and
  (f) stabilizing the condition of the treated hair by applying thereto a bonding composition comprising a water solution of a cationic thermosetting aminopolyamide-epichlorohydrin resin.

2. A combination of compositions for relaxing natural curls from hair on a human head, comprising:
  (a) a first composition containing a blend of water and ammonium bisuflite having a pH less than about 7 and more than about 5, which when applied to hair has the capacity of reducing the disulfide linkages in the hair keratin;

(b) a second composition containing a blend of water and a weak alkaline substance having a pH not greater than about 9, and when applied to the hair after treatment with said first composition has the capacity of chemically neutralizing the said first composition; and (c) a third composition containing a water solution of a cationic thermosetting aminopolyamide-epichlorohydrin resin when applied to hair after the successive treatments of said first and said second compositions stabilizes the condition of the treated hair.

3. A combination of compositions for relaxing natural curls from hair on a human head, comprising:

(a) a first composition containing a blend of water and a salt of a weak acid having a pH less than about 7, but more than about 5, and having the capacity of reducing the disulfide linkages of the hair keratin;

(b) a second composition containing a blend of water and a weak alkaline substance having a pH not greater than about 9, and when applied to the hair after treatment with said first composition has the capacity of chemically neutralizing the said first composition; and (c) a third composition containing a water solution of a thermosetting aminopolyamide resin which when applied to hair after the successive treatments of said first and said second compositions stabilizes the condition of the treated hair.

* * * * *